US00PP07819P

United States Patent [19]

Meilland

[11] Patent Number: Plant 7,819

[45] Date of Patent: Mar. 10, 1992

[54] ROSE PLANT—MEINIACIN VARIETY

[75] Inventor: Alain A. Meilland, Antibes, France

[73] Assignee: The Conard-Pyle Company, West Grove, Pa.

[21] Appl. No.: 580,261

[22] Filed: Sep. 10, 1990

[51] Int. Cl.[5] ..... A01H 5/00

[52] U.S. Cl. ..... Plt./19

[58] Field of Search ..... Plt. 11, 18, 19, 20

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly and continuously forms attractive very double long lasting blossoms which are Rose Bengal in coloration. The blossoms maintain their coloration well throughout the blooming process and possess a strong fragrance. The plant exhibits a very upright growth habit, forms vigorous vegetation, and is well suited for service as attractive ornamentation in parks and gardens. Additionally, the plant is not particularly affected by cryptogamic diseases.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the Meilista variety (nonpatented in the United States). The male parent (i.e., the pollen parent) was the product of the cross of the Meichim variety (nonpatented in the United States) and the Silvia variety (nonpatented in the United States). The parentage of the new variety can be summarized as follows:

Meilista × (Meichim × Silvia).

The seeds resulting from the above pollination were sown and 40 small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance on a continuous basis attractive long lasting very double blossoms which are Rose Bengal in coloration,
(b) forms blossoms which maintain their coloration well,
(c) forms blossoms which are fragrant throughout the flowering process,
(d) exhibits vigorous vegetation,
(e) exhibits a very upright growth habit,
(f) is particularly suited for growing in parks and gardens, and
(g) is not particularly affected by cryptogamic diseases.

The new variety presents a very clean and decorative overall appearance.

The new variety well meets the needs of the horticultural industry and is particularly well suited for use as attractive ornamentation in the landscape.

The new variety has been found to undergo asexual propagation by a number of conventional routes, including budding, grafting, and cuttage. Asexual reproduction by the above mentioned methods as performed in France shows that the characteristics of the new variety are strictly transmissible from one generation to another and appear to be firmly fixed.

The new variety has been named the Meiniacin variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during September while budded on *Rosa froebelli* understock and growing outdoors at LeCannet-des-Maures, Var, France.

DETAILED DESCRIPTION

Figures 1, 2, 3, 4, 5, 6, 7, 8, 9, 10, 11, 12, 13, 14, 15:
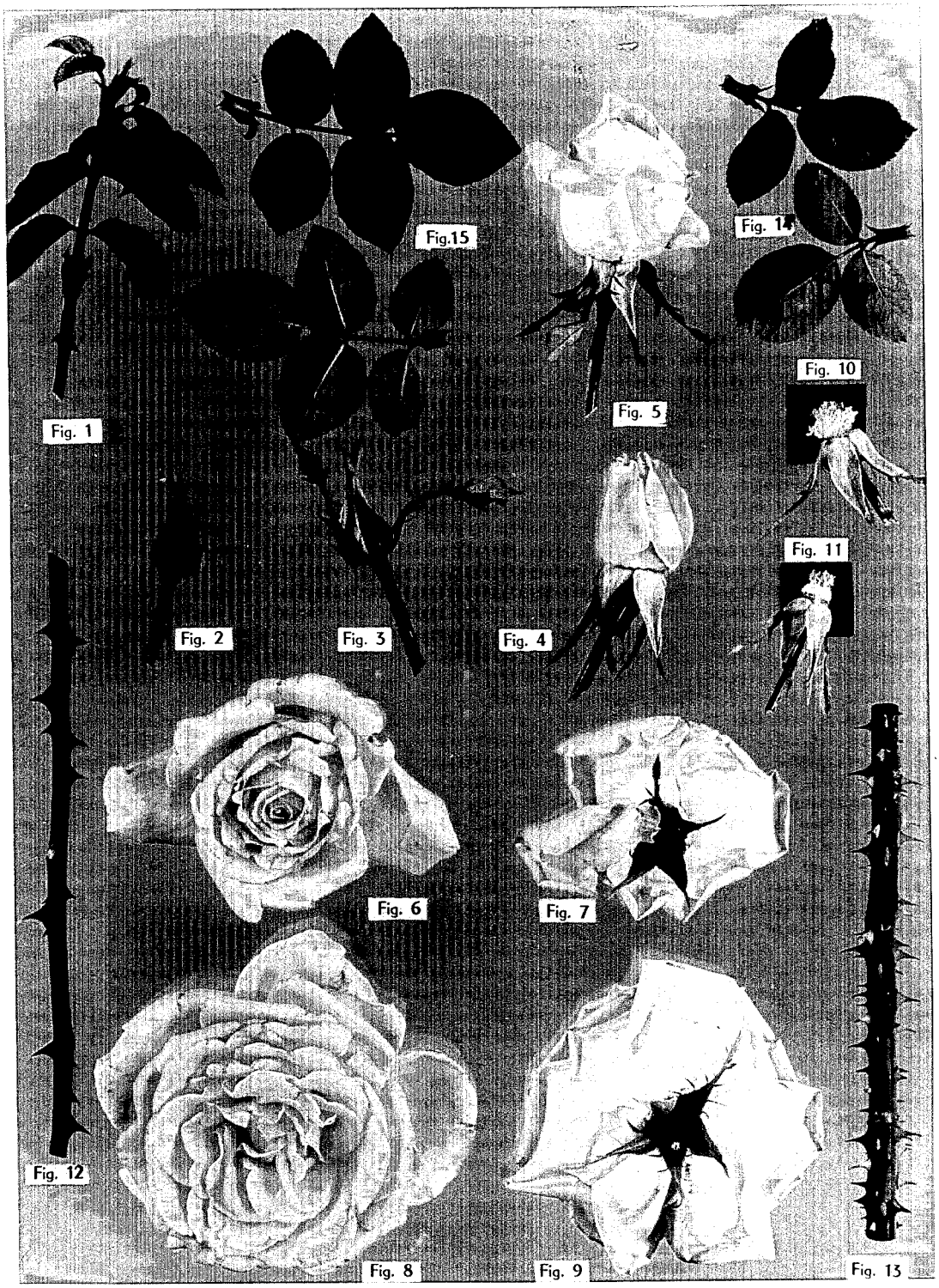
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower — plan view — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of leaves with three leaflets — plan view — upper surface (top) and lower surface (bottom)
FIG. 15 illustrates specimens of leaves with five leaflets — plan view — upper surface (top) and lower surface (bottom).

The chart used in the identification of the colors is that of The Royal Horticultural Society (R.H.S. Colour Chart). The description is based on the observation of two year old plants made during September while budded on *Rosa froebelli* understock and growing in outdoors at LeCannet-des-Maures, Var, France. The coloration in common terms precedes reference to the chart.

Class: Hybrid Tea.

Plant:

*Height.*—Approximately 100 to 110 cm. on average.

*Habit.*—Very upright.

Branches:

*Coloration.*—Young stems: light green, Yellow-Green Group 144A, widely stained with reddish brown. Adult wood: medium green, Yellow-Green Group 146B.

*Thorns.*—Size: average. Quantity: numerous. Color: pinkish green on young stems and greenish changing to tan on mature wood.

Leaves:

*Stipules.*—Adnate, pectinate, very wide and linear.

*Petioles.*—Upper surface: striped reddish brown on young foliage and medium green on adult foliage with more or less glandular edges. Under surface: light green, bear only a very few prickles.

*Leaflets.*—Number: 3 and 5. Sometimes the first pair of leaflets is incompletely formed. Shape: oval. Serration: single and regular. Texture: leathery. General appearance: dense, semi-dull foliage. Color (young foliage): Upper surface: reddish-brown in coloration. Under surface: reddish. Color (adult foliage): Upper surface: dark green, Green Group 137A. Under surface: light green, Green Group 137C.

Inflorescence:

*Number of flowers.*—Usually one single bloom per stem.

*Peduncle.*—Short, rigid, light green and widely stained with reddish coloration, bears numerous prickles. The length is approximately 5 to 6 cm. on average.

*Sepals.*—Upper surface: tomentose, greenish in coloration. Under surface: medium green and more or less stained with reddish coloration, more or less glandular, and the outer sepals have appendiculate edges which end with a fairly well developed leaf-like appendix.

*Buds.*—Shape: conical. Length: approximately 2.5 to 3 cm. on average. Size: average. Color upon opening: Upper surface: China Rose, Red-Purple Group 58B. Under surface: China Rose, Red-Purple Group 58B.

*Flower.*—Shape: cup-like and fully double. Diameter: approximately 13 to 14 cm. on average. Color (when opening begins): Upper surface: Rose Bengal, Red-Purple Group 57C. Under surface: light Rose Bengal, Red-Purple Group 57D. Color (when blooming): Upper surface: Rose Bengal, Red-Purple Group 57C. Under surface: light Rose Bengal, Red-Purple Group 57D. Color (at end of opening): Upper surface: Rose Bengal, Red-Purple Group 57C. under surface: light Rose Bengal, Red-Purple Group 57D. Fragrance: strong. Lasting quality: long. Petal number: approximately 36 to 43 on average. Petal shape: rounded to oval. Texture: consistent. Petal drop: good. Stamen number: approximately 40 to 45 on average. Anthers: ochre, normal, located below the pistils. Filaments: free standing, light fuschia in coloration, of irregular heights. Pistils: approximately 92 to 97 on average. Stigmas: normal, straw colored. Styles: dark fuschia, tomentose at base, and sometimes bonded together. Receptacle: in longitudinal section it is wide and in the shape of a funnel.

Development:

*Vegetation.*—Vigorous.

*Blooming.*—Very abundant and continuous.

*Aptitude to bear fruits.*—Poor.

*Resistance to frost.*—Good.

*Resistance to diseases.*—Good.

I claim:

1. A new and distinct variety of Hybrid Tea rose plant characterized by the following combination of characteristics:

(a) forms in abundance on a continuous basis attractive long lasting very double blossoms which are Rose Bengal in coloration,
(b) forms blossoms which maintain their coloration well,
(c) forms blossoms which are fragrant throughout the flowering process,
(d) exhibits vigorous vegetation,
(e) exhibits a very upright growth habit,
(f) is particularly suited for growing in parks and gardens, and
(g) is not particularly affected by cryptogamic diseases;

substantially as herein shown and described.

* * * * *